(12) United States Patent
Labyt

(10) Patent No.: US 12,303,272 B2
(45) Date of Patent: May 20, 2025

(54) MULTI-MODAL 3D MARKER FOR CO-REGISTRATION OF BIOMAGNETIC AND MAGNETIC RESONANCE IMAGING

(71) Applicant: COMMISSARIAT A L'ENERGIE ATOMIQUE ET AUX ENERGIES ALTERNATIVES, Paris (FR)

(72) Inventor: Etienne Labyt, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 75 days.

(21) Appl. No.: 18/267,060

(22) PCT Filed: Dec. 8, 2021

(86) PCT No.: PCT/EP2021/084788
§ 371 (c)(1),
(2) Date: Jun. 13, 2023

(87) PCT Pub. No.: WO2022/128683
PCT Pub. Date: Jun. 23, 2022

(65) Prior Publication Data
US 2024/0041373 A1     Feb. 8, 2024

(30) Foreign Application Priority Data
Dec. 17, 2020  (FR) ........................................ 2013422

(51) Int. Cl.
*A61B 5/243*   (2021.01)
*A61B 5/00*    (2006.01)
*A61B 5/245*   (2021.01)

(52) U.S. Cl.
CPC .............. *A61B 5/243* (2021.01); *A61B 5/245* (2021.01); *A61B 5/6814* (2013.01); *A61B 5/6823* (2013.01)

(58) Field of Classification Search
CPC .. A61B 5/245; A61B 5/243; A61B 2034/2051
See application file for complete search history.

(56) References Cited

U.S. PATENT DOCUMENTS

2017/0352457 A1   12/2017  Kubota et al.
2020/0100695 A1*   4/2020  Misaka ................... A61B 5/055
(Continued)

FOREIGN PATENT DOCUMENTS

FR        3 056 761 A1      3/2018

OTHER PUBLICATIONS

Messaritaki et al., "Assessment and elimination of the effects of head movement on MEG resting-state measures of oscillatory brain activity," (Oct. 1, 2017), Neuroimage, 159:302-324). (Year: 2017).*

(Continued)

*Primary Examiner* — Jeffrey G Hoekstra
*Assistant Examiner* — Ashish S Jasani
(74) *Attorney, Agent, or Firm* — BakerHostetler

(57) ABSTRACT

A device for improving the precision of a biomagnetic image of a patient is provided. The device comprises a covering, a plurality of markers and at least five three-axis coils. Three-axis coils and markers of the plurality of markers are placed at the same location on the covering so that, when the covering is positioned on the patient, singular points of the part of the patient can be detected by magnetic resonance imaging and by biomagnetic imaging (MEG, MCG).

8 Claims, 7 Drawing Sheets

(56) References Cited

U.S. PATENT DOCUMENTS

2020/0305747 A1* 10/2020 Kudo .................. A61B 5/245
2021/0267678 A1* 9/2021 Oshima ............. A61B 18/1492

OTHER PUBLICATIONS

Hill et al., "Multi-channel whole-head OPM-MEG: Helmet design and a comparison with a conventional system," (Oct. 1, 2020), NeuroImage vol. 219. (Year: 2020).*
McGowin, "Head Motion Evaluation and Correction in Magnetoencephalography," (May 2015), PhD. Dissertation Physics, Wake Forest University, <https://wakespace.lib.wfu.edu/bitstream/handle/10339/57118/McGowin_wfu_0248D_10696.pdf>. (Year: 2015).*
"Module: Digitalization HPI coils and anatomical landmarks why and how," (Sep. 5, 2016), <https://natmeg.se/to_download/HPImodule_v1.1.pdf>). (Year: 2016).*
Chella et al., "The impact of improved MEG-MRI co-registration on MEG connectivity analysis," (Aug. 15, 2019) NeuroImage, vol. 197, Aug. 15, 2019, pp. 354-367. (Year: 2019).*
Pfeiffer, et al., "On-scalp MEG sensor localization using magnetic dipole-like coils: A method for highly accurate co-registration", NeuroImage, vol. 212, 116686, 2020.

* cited by examiner

MULTI-MODAL 3D MARKER FOR CO-REGISTRATION OF BIOMAGNETIC AND MAGNETIC RESONANCE IMAGING

CROSS-REFERENCE TO RELATED APPLICATIONS

This application is a National Stage of International patent application PCT/EP2021/084788, filed on Dec. 8, 2021, which claims priority to foreign French patent application No. FR 2013422, filed on Dec. 17, 2020, the disclosures of which are incorporated by reference in their entirety.

FIELD OF THE INVENTION

The present invention relates to a device for improving the precision of a biomagnetic image, and to an associated method.

BACKGROUND

A number of medical imaging techniques exist today for obtaining information on a part of a patient's body.

Magnetic resonance imaging, or MRI, is a medical imaging technique that makes it possible to obtain two-dimensional or three-dimensional views of the inside of the body non-invasively and with relatively high contrast resolution. The principle of MRI is based on the phenomenon of nuclear magnetic resonance relating to the coupling between the magnetic moment of a nucleus of an atom and the external magnetic field. MRI requires a strong and stable magnetic field produced by a superconducting magnet which creates tissue magnetization by aligning the magnetic spin moments. Weaker oscillating magnetic fields, or radiofrequency, are then applied so as to slightly modify this alignment and to produce a phenomenon of precession, which gives rise to a measurable magnetic signal. MRI is mainly dedicated to the imaging of soft tissues (brain, muscles, heart, lungs and viscera) and tumors.

Biomagnetic imaging is a technique of imaging the magnetic fields generated by the human body. It thus makes it possible to measure magnetic fields induced by the electrical activity of different parts of the body with a view to obtaining biomagnetic data. In biomagnetic imaging, there is what is called magnetoencephalography (MEG). This MEG technique is employed with a clinical objective in neurology and also in research in cognitive neurosciences, and it provides biomagnetic data in the form of MEG data. In biomagnetic imaging, there is also what is called magnetocardiography (MCG). This MCG technique is used in cardiology. As the measured magnetic fields are extremely weak, MEG and MCG use equipment based on SQUID (Superconducting Quantum Interference Device) sensors cooled by a cryogenic fluid within a Dewar. In the case of analysis relating to the brain, the SQUID sensors are positioned a few centimeters from the patient's head and are fixed in this position. This distance of the sensors, imposed by the use of the cryogenic fluid, affects the quality of the measured signal. The patient's head may also move in relation to these sensors, which also affects the precision of the imaging performed by MEG. In order to solve this problem, research work has been carried out on performing magnetoencephalography using optically pumped magnetometers. All of the research in this field is based on magnetometers with optical pumping of alkali atoms. There is another category of optically pumped magnetometers based on helium. A support helmet is known which allows each magnetometer to be positioned as close as possible to the patient's head. In the case of optically pumped helium magnetometers, a procedure of self-location of these magnetometers directly provides the positions and the orientations of the magnetometers relative to one another on the patient's head. The document FR3056761 discloses a method for mutual calibration of the various optically pumped helium magnetometers in order to enable them to self-locate.

In order to locate the active regions of the patient's body that are at the origin of electrical activity, for example the brain, it is necessary to merge data from magnetoencephalography with anatomical data resulting from magnetic resonance imaging, so as to obtain a combined image. This is done by registering the position of the MEG sensors (SQUID or optically pumped alkali magnetometers) in the coordinate system in which the volume reconstructed from MRI is referenced. Currently, the MEG data are merged with MRI data in two steps. In a first step, singular points such as bony prominences, the nasion, the right and left pre-auricular points, etc., are located using an external optical or electromagnetic system at the time of recording of the MEG data. This makes it possible to register the position of the MEG sensors relative to the patient's head. In a second step, a 3D reconstruction of the anatomy is performed with identification of the same singular points on the MRI images. The singular points are thus located by two different means in MRI and in MEG.

However, the step of registering the position of the magnetometers with respect to the position of the head and the step of merging MEG and MRI data are both sources of bias which affect the precision of functional localization in MEG.

There is therefore a need to improve this procedure of registering and merging MEG/MRI data by means of a device making it possible to obtain medical imaging of greater precision.

SUMMARY OF THE INVENTION

The present invention aims to meet this need.

More particularly, the present invention makes available a device which aims to improve the procedure of registering/merging the MEG/MRI or MCG/MRI data in order to obtain a medical image having greater precision.

A first subject of the invention is a device for improving the precision of a biomagnetic image of a patient. This device comprises a covering adapted to be positioned on an anatomical part of the patient. The device comprises a plurality of markers arranged on the covering, the markers being adapted to create a contrast when obtaining an image of the patient produced by magnetic resonance imaging. The device also comprises at least five three-axis coils, each three-axis coil being adapted to emit a magnetic field, the magnetic fields of the three-axis coils being detectable by a set of optically pumped magnetometers during an examination by biomagnetic imaging. These three-axis coils are arranged on the covering in such a way that, when the device is positioned on the patient, each of these three-axis coils is located on a singular point of the patient. In addition, the three-axis coils and markers of the plurality of markers are placed at the same location on the covering so that, when the covering is positioned on the patient, singular points of the part of the patient are detectable by magnetic resonance imaging and by biomagnetic imaging. The device comprises supports, each support having a first reception zone adapted to receive one of the markers and a second reception zone adapted to receive one of the three-axis coils. The marker and the three-axis coil are then placed at the same location on the covering. The second reception zone comprises a protuberance adapted to be housed in an associated cavity of the three-axis coil. The protuberance comprises a main body and a pin extending from the main body. The protuberance has the role of an indexing device for positioning the three-axis coil in the support.

The device is designed to be worn by the patient in both imaging modes: biomagnetic and MRI. It therefore facilitates the use of the data obtained by these two medical imaging modes. The three-axis coils are co-located with markers on the covering at the same singular points. This ensures optimum registration of MEG/MRI data or of MCG/MRI data in order to obtain a combined medical image having high precision.

The three-axis coils and the markers are positioned in a common support attached to the covering of the device. These coils and these markers are thus co-located in a precise, simple and practical manner, at the level of the singular points on the patient.

The three-axis coil is also effectively maintained in the support of the covering.

This also ensures precise and reproducible orientation of the three axes of the coil.

In a particular embodiment, the covering is made of a flexible biocompatible silicone material.

In a particular embodiment, the marker comprises gadolinium and/or a plurality of superparamagnetic nanoparticles.

In a particular embodiment, each marker has the shape of a pellet having a diameter of less than or equal to 6 mm.

In a particular embodiment, the device is positioned on the face of the patient, or the device is positioned on the torso of the patient.

Another subject of the invention is a method for improving the precision of a biomagnetic image of a patient, the method comprising a step of applying to a part of the patient a device according to the above subject matter. This device comprises a plurality of three-axis coils, each three-axis coil being adapted to emit a magnetic field, the magnetic fields of the three-axis coils being detectable by a set of optically pumped magnetometers during a biomagnetic imaging examination. The method also comprises a biomagnetic imaging examination step for obtaining biomagnetic data, the examination step comprising a step of self-referencing of the position of the optically pumped magnetometers with respect to the three-axis coils. In addition, the method comprises a magnetic resonance imaging examination step for obtaining MRI data. Finally, this method comprises a step of merging the biomagnetic data with the MRI data by simple matching of the common positions acquired precisely during the biomagnetic imaging examination step and the MRI examination step.

This makes it possible to obtain a combined medical image of the part of the patient concerned, by overcoming the registration and fusion bias of the prior art.

In a particular embodiment, the biomagnetic imaging examination is a magnetoencephalography examination for obtaining MEG data or a magnetocardiography examination for obtaining MCG data.

In a particular embodiment, the optically pumped magnetometers are optically pumped helium magnetometers.

BRIEF DESCRIPTION OF THE DRAWINGS

The present invention will be better understood on reading the detailed description of embodiments given as non-limiting examples and illustrated in the accompanying drawings, in which.

In the various figures, identical or similar elements bear the same references.

DETAILED DESCRIPTION

Figure 1:
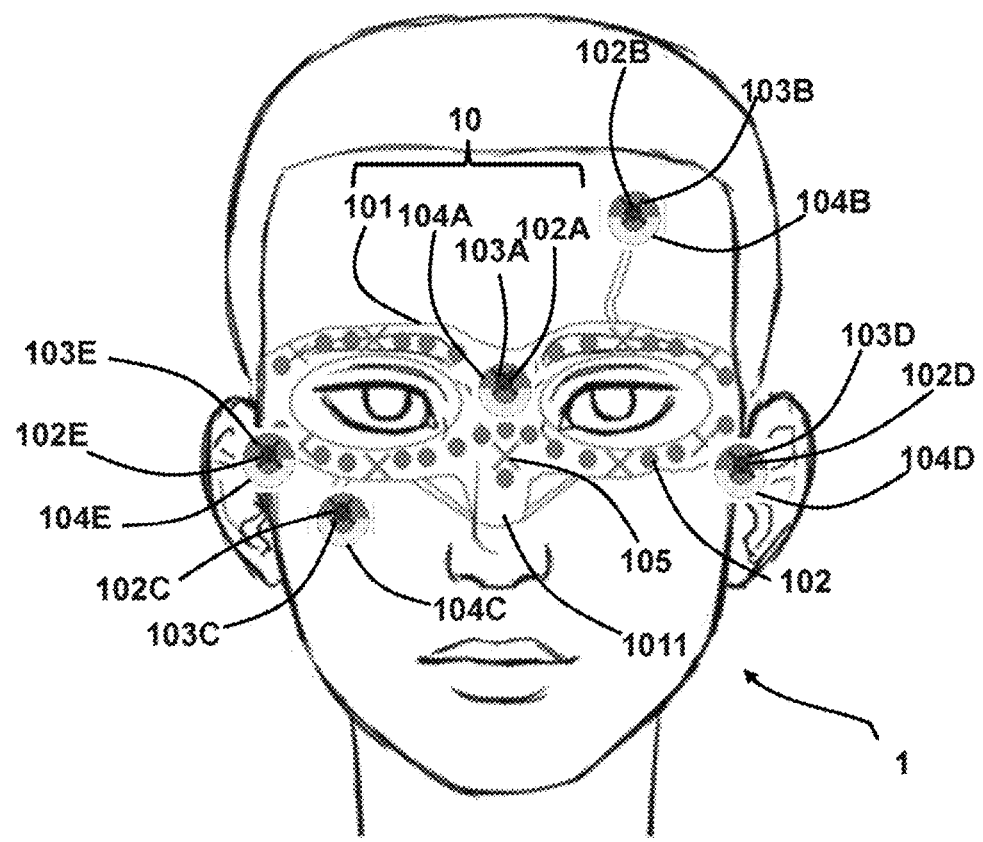
FIG. 1 is a front view of the face of a patient wearing the device according to a first application of the invention.
Figure 2:
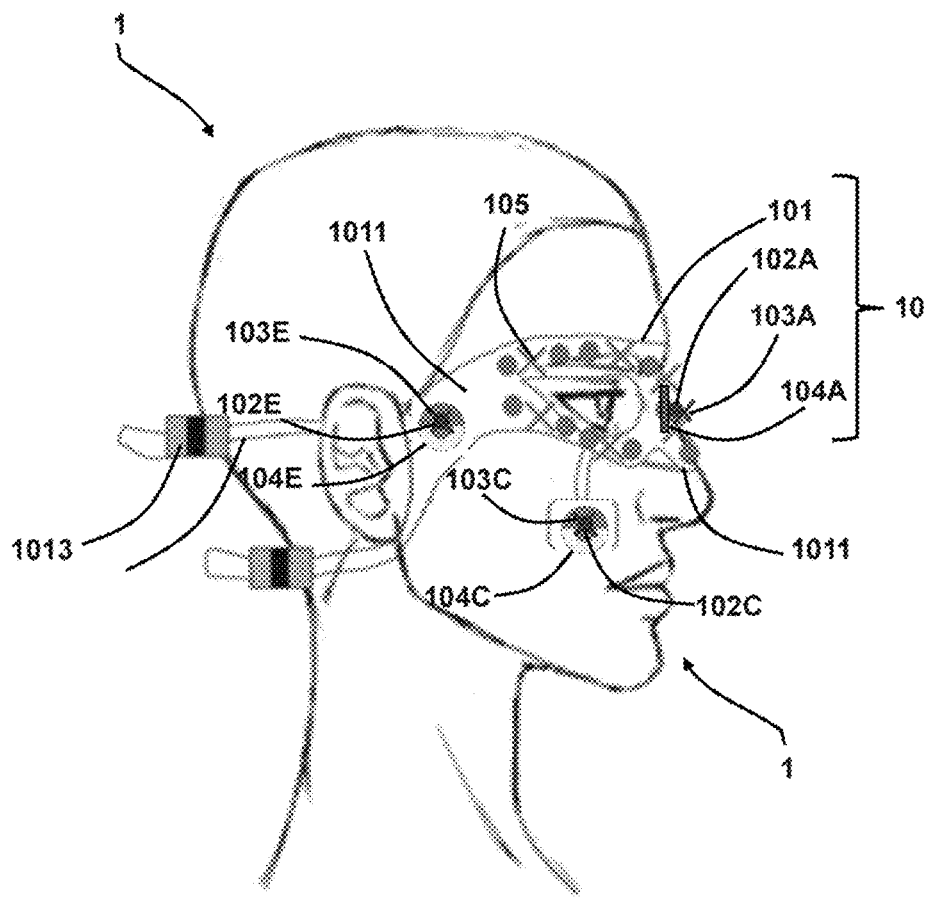
FIG. 2 is a profile view of the face of the patient from FIG. 1.

FIGS. 1 and 2 show the face of a patient wearing a device 10 for obtaining a medical image of the patient's brain. The device 10 comprises:
- a covering 101;
- a plurality of markers 102, 102A, 102B, 102C, 102D, 102E arranged on the covering;
- a plurality of three-axis coils 103A, 103B, 103C, 103D, 103E arranged on the covering;
- supports 104A, 104B, 104C, 104D, 104E for receiving all or some of the markers 102, 102A, 102B, 102C, 102D, 102E and three-axis coils 103A, 103B, 103C, 103D, 103E.

The covering 101 is presented here in the form of a mask adapted to be positioned on the upper part of the patient's face 1 around the eyes, so as to cover the singular points of interest for MEG imaging. The covering 101 comprises a main part 1011, elastic laces 1012 and an adjustment device 1013. The main part 1011 is adapted to lie flat on the face 1 of the patient. This main part 1011 is configured to carry the plurality of markers 102, 102A, 102B, 102C, 102D, 102E and the plurality of three-axis coils 103A, 103B, 103C, 103D, 103E. The elastic laces 1012 are adapted to apply stress to the covering in order to adapt the latter to the shape of the patient's face. This makes it possible to maintain the markers 102, 102A, 102B, 102C, 102D, 102E and the plurality of three-axis coils 103A, 103B, 103C, 103D, 103E as close as possible to the bony prominences of the face (orbital arches, zygomatic arches, etc.). In addition, the main part 1011 of the covering 101 that covers the nose is tensioned by elastic laces 1012. In a particular embodiment, the covering 101 comprises two elastic laces 1012, and this allows the covering 101 to be tightened at the back of the patient's head. A first elastic lace passes, for example, above one ear and the second elastic lace passes below the other ear. The adjustment device 1013 is adapted to adjust and maintain the elastic laces 1012 pressed against the back of the head. It improves patient comfort during the magnetic resonance imaging examination, the patient being in a lying position for this examination. This adjustment device 1013 is, for example, of the same type as a conventional adjustment device used for a backpack. Alternatively, the laces 1012 are not elastic. They are simple cords that are adjusted using the adjustment device 1013.

The main part 1011 and the elastic laces 1012 of the covering 101 are made of a flexible silicone material, for example 50 Shore translucent talc silicone. This material is notably biocompatible and MRI compatible.

In an alternative embodiment, the covering 101 is of the diving mask type.

The markers 102, 102A, 102B, 102C, 102D, 102E are adapted to create a contrast when obtaining images of the face of the patient wearing the covering 101, during a magnetic resonance imaging operation. These markers 102, 102A, 102B, 102C, 102D, 102E here have the shape of a pellet having a diameter of less than or equal to 6 mm. These pellets are, for example, pellets of the MRI pin point ref 187 type from the supplier Beekley Medical®. In a particular embodiment, the markers 102, 102A, 102B, 102C, 102D, 102E contain gadolinium. As a variant, the markers 102, 102A, 102B, 102C, 102D, 102E contain, in addition to or as a replacement for gadolinium, a plurality of superparamagnetic nanoparticles. The expression "superparamagnetic nanoparticles" is understood as meaning a ferromagnetic or ferrimagnetic material having grains of nanometric dimensions. In the example of FIGS. 1 and 2, the device comprises more than twenty markers 102, 102A, 102B, 102C, 102D, 102E regularly distributed over the main part 1011 of the covering 101. More particularly, the markers 102, 102A, 102B, 102C, 102D, 102E are present on the orbital arches, the zygomatic arches and a bony wing of the nose. This makes it possible to refine the location of the mask on the MRI images.

The three-axis coils 103A, 103B, 103C, 103D, 103E are adapted to emit a magnetic field. The expression "three-axis coil" is understood as meaning a coil adapted to emit magnetic fluxes along three mutually perpendicular axes. Such a coil is, for example, a Helmholtz coil. Here, the three-axis coils 103A, 103B, 103C, 103D, 103E are of small dimensions in order to be carried by the covering 101. They are represented by crosses in FIG. 1. The magnetic field emitted by the three-axis coils is detectable by a set of optically pumped magnetometers during a magnetoencephalography examination. The optically pumped magnetometers are in the form of small capsules which are organized in the form of a helmet (not shown in FIGS. 1 and 2) fitted on the upper part of the patient's head. Such a helmet can comprise 20 to 200 regularly distributed magnetometers. The optically pumped magnetometers are able to measure the intensity and/or the direction of a magnetic field. Each magnetometer comprises an internal element sensitive to such a magnetic field. This internal element associated with an electronic device makes it possible to extract the measurement from the magnetic field.

In the embodiment of FIGS. 1 and 2, the covering 101 comprises five three-axis coils designated 103A, 103B, 103C, 103D, 103E. Thus, a first three-axis coil 103A is placed at the top of the patient's nose. A second three-axis coil 103B is arranged on the patient's forehead. A third three-axis coil 103C is placed on the patient's right cheek. The fourth three-axis coil 103D and the fifth three-axis coil 103E are placed at the level of the left and right pre-auricular points (in front of the ears). The second three-axis coil 103B and the third three-axis coil 103C make it possible to improve the precision of registration of the optically pumped magnetometers. In addition, the third three-axis coil 103C makes it possible, in magnetic resonance imaging, to identify the right from the left without error, regardless of the radiological or neurological convention used to view the MRI images. Other three-axis coils 103 are present on other singular points of the patient's face, such as on the orbital arches, the zygomatic arches or the wing of the nose. These additional three-axis coils make it possible to further improve the precision in the registration of the MEG and MRI data obtained. In a particular embodiment, the device 10 comprises at least five three-axis coils.

Figure 3:
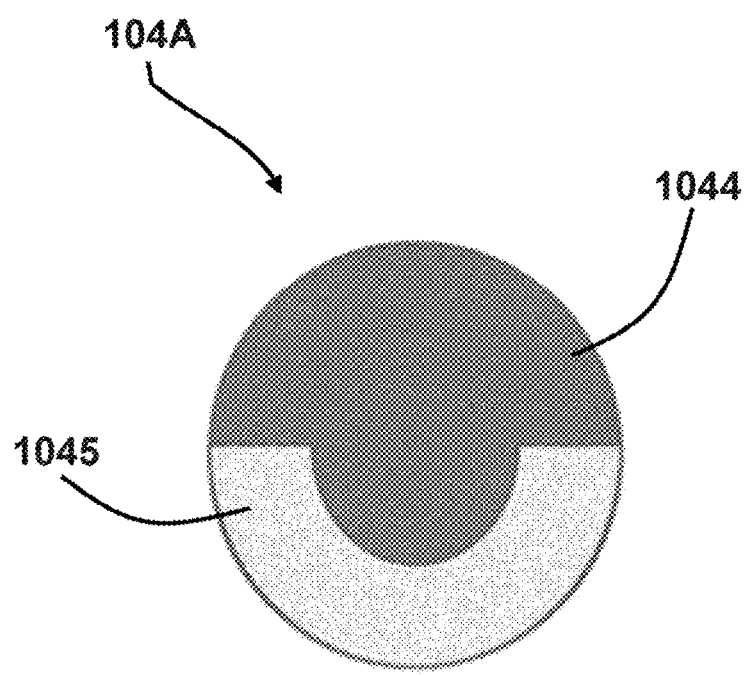
FIG. 3 is a front view of a support adapted to be attached to the device from FIG. 1.
Figure 4:
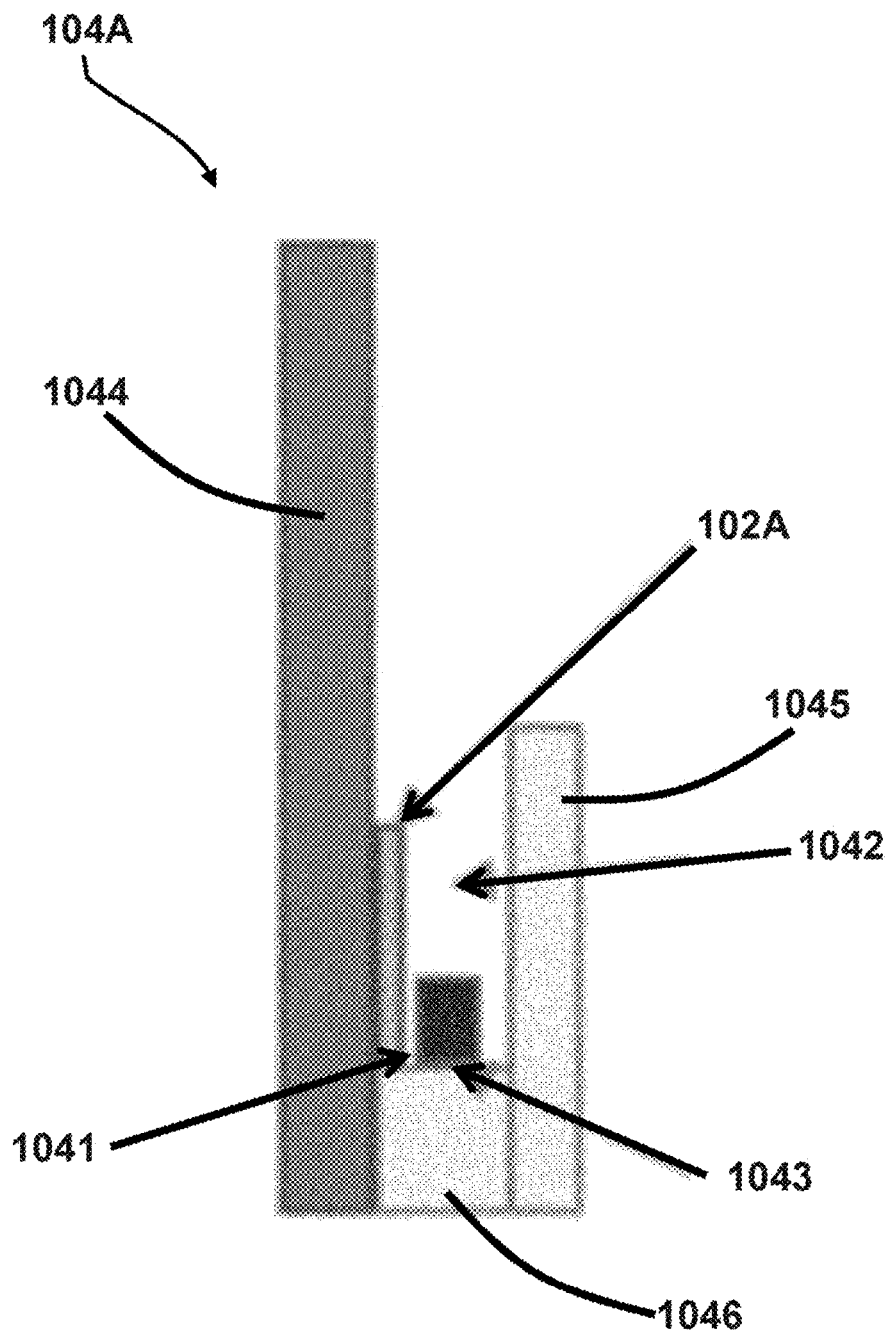
FIG. 4 is a side view of the support from FIG. 3.
Figure 5:
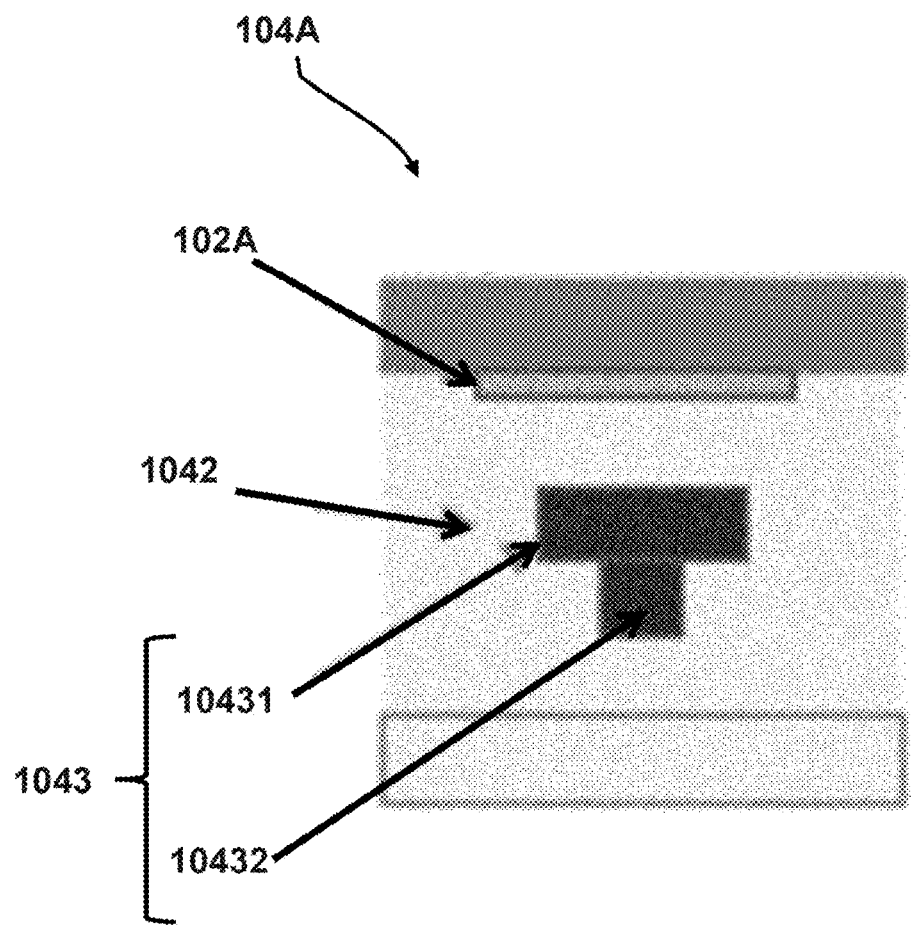
FIG. 5 is a top view of the support from FIG. 3.

The supports 104A, 104B, 104C, 104D, 104E are adapted to receive markers 102A, 102B, 102C, 102D, 102E and three-axis coils 103A, 103B, 103C, 104D, 104E. By way of example, the support 104A in particular is shown in FIGS. 3 to 5. This support 104A comprises:
  a rear part 1044;
  a front part 1045;
  an intermediate part 1046.

The rear part 1044 is adapted to attach to the covering 101 in order to hold the support 104 there. This rear part 1044 is a disk having a diameter of greater than 6 mm.

The front part 1045 is adapted to hold one of the three-axis coils in the support 104A. This front part 1045 has a half-ring shape of identical diameter to the rear part 1044. This half-ring shape makes it possible to maintain the marker and the three-axis coil present in the support 104A.

The intermediate part 1046 is arranged between the rear part 1044 and the front part 1045 of the support 104A.

The rear part 1044, the front part 1045 and the intermediate part 1046 define the spaces in which the three-axis coil and the associated support will be housed. Thus, the support 104A comprises a first reception zone 1041 and a second reception zone 1042. The first reception zone 1041 is adapted to receive a marker 102A. This first reception zone 1041 is delimited by the rear part 1044 of the support 104A and by a protuberance 1043. The second reception zone 1042 is delimited by the marker 102A and by the front part 1045. The protuberance 1043 is adapted to be housed in an associated cavity in the three-axis coil. In Figure the protuberance 1043 comprises a main body 10431 and a pin 10432. The main body 10431 makes it possible to fix the three-axis coil in the support while avoiding any rotation thereof in the support. The pin 10432 extends from the main body 10431. Its role is to avoid any error in the placement of the three-axis coil within the support 104, which makes it possible to place the axes of the three-axis coil always the same way. The above description also applies to the other supports 104B, 104C, 104D, 104E.

In the example of FIG. 1, the device 10 comprises five supports 104A, 104B, 104C, 104D, 104E. Alternatively, the device 10 comprises more than five supports. These other supports are, for example, positioned at the level of the crosses 105 of the device 10 which are visible in FIGS. 1 and 2.

Figure 6:
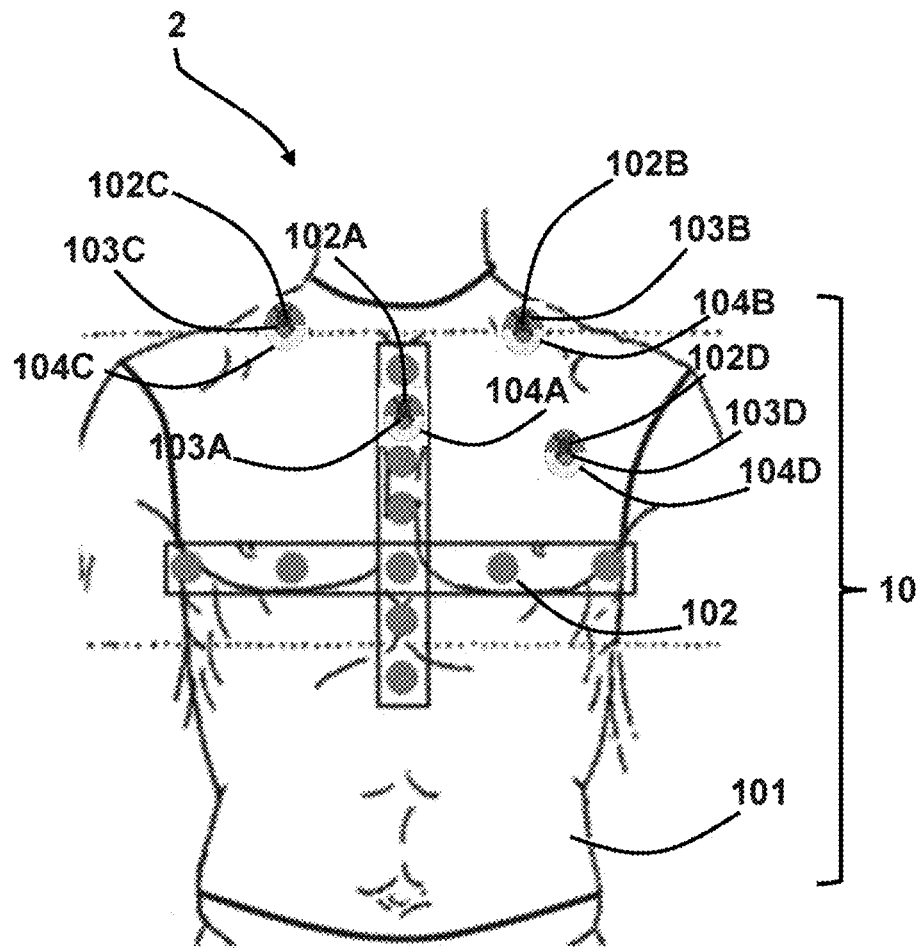
FIG. 6 is a front view of the torso of a patient wearing the device according to a second application of the invention.

FIG. 6 illustrates the torso 2 of the patient wearing the device 10 in a second application of the invention. In this embodiment, the device 10 comprises a covering 101 in the form of a thoracic vest for biomagnetic imaging of the heart with localization of the foci at the origin of cardiac arrhythmias. In this second application of the invention, it is a matter of registering the magnetocardiography data with the 3D MRI data of the heart. To do this, markers 102 are regularly distributed on the covering 101. These markers 102 form a cross, the center of which is situated between the two pectorals of the patient. On an upper part of this cross, more precisely at the top of the patient's sternum, the covering comprises a first support 104A. This support 104A is adapted to carry a marker 102A and also a three-axis coil 103A. Other supports 104B, 104C are also positioned on the patient's collar bones. Another support 104D is positioned at the level of the left pectoral. The device 10 is adapted here to obtain a combined image of the patient's heart. In order to detect any dysfunction of this heart, it is possible to carry out in succession a magnetocardiography examination in order to obtain MCG data and a magnetic resonance imaging examination in order to obtain MRI data.

It will be noted that, in this second application of the invention, it is not necessary to equip the patient with a helmet carrying optically pumped magnetometers. These optically pumped magnetometers will be carried directly by the thoracic vest.

It will also be noted that the patient's back can comprise a plurality of supports carrying markers and three-axis coils for performing MCG and MRI examinations in order to improve the precision of the imaging.

Figure 7:
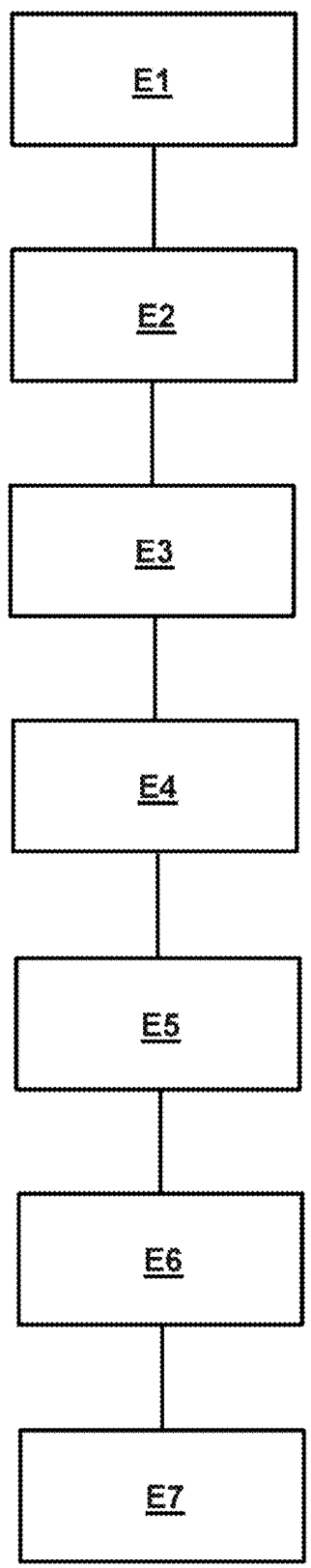
FIG. 7 is a diagram illustrating the different steps of a method for obtaining a medical image of a patient wearing the device from FIGS. 1 to 6.

FIG. 7 illustrates the different steps of a method for improving the precision of a biomagnetic image of the patient wearing the device from FIGS. 1 to 2 for magnetoencephalography, or the device from FIG. 6 for magnetocardiography.

In a first step E1, the device 10 is positioned on the patient. If it is desired to obtain information on the brain, this device 10 is positioned on the face 1 of the patient. Alternatively, if it is the heart that is the subject of the examination, the device 10 is positioned on the torso 2 of the patient.

In a second step E2, a helmet comprising the optically pumped magnetometers is positioned on the patient's head. In the case of magnetocardiography, the optically pumped magnetometers are positioned on the patient's torso in the form of a matrix.

In a third step E3, the three-axis coils 103A, 103B, 103C of the device 10 are activated.

In a fourth step E4, the positions of the optically pumped magnetometers are determined with respect to the three-axis coils. These positions are determined without any external system. As the three-axis coils are present at singular points of the patient, the optically pumped magnetometers are then positioned automatically with respect to these singular points. The self-locating of the position of the optically pumped magnetometers with respect to the position of these three-axis coils is thus carried out. It will be noted that, in a preferred embodiment of the invention, the magnetometers are optically pumped helium magnetometers.

In a fifth step E5, the MEG data or the MCG data are acquired during the magnetoencephalography examination or the magnetocardiography examination. These data streams are recorded during several recording sequences.

In a sixth step E6, a step of magnetic resonance imaging examination is performed in order to obtain MRI data (three-axis coils are removed beforehand from the supports). The markers arranged on the device 10 remain in place and allow the identification of the same singular points as those located by the MEG examination or the MCG examination using the coils.

In a seventh step E7, the MEG data or the MCG data and the MRI data are processed in order to be merged by matching the coordinates of common singular points acquired in the two modalities. It is then possible to obtain a combined image that can be used by a practitioner. This combined image makes it possible to visualize the variations of electrical fields reconstructed from the magnetoencephalography or the magnetocardiography in the volume generated by the examination by magnetic resonance imaging.

The device forming the subject of the invention affords the following advantages:

it makes it possible to provide a support of the mask or vest type, making it possible to position, in common supports, three-axis emitting coils and gadolinium pellets visible on the MRI images;

it makes it possible to use the measurement of the magnetic field emitted by the three-axis coils, by the optically pumped magnetometers present on the head or on the chest of the patient;

it makes it possible to exploit the co-location of the three-axis coils visible in MEG or in MCG and of the gadolinium pellets visible in MRI, on account of their common support, for the registration of the MEG/MRI or MCG/MRI data. The use of common supports for the emitter coils and the gadolinium pellets ensures optimal registration between the MEG/MCG and MRI data since the same points will be located exactly with both techniques;

the measurement of the magnetic field emitted by the three-axis coils allows self-locating of each optically pumped helium magnetometer sensor;

the use of a mask adjusted to the patient's face or of a vest on the patient's thorax, usable both in MEG/MCG (with the three-axis coils allowing location) and in MRI (with the pellets of gadolinium), greatly limits the sources of bias during MEG/MCG registration with MRI, since the position of the coils and of the gadolinium pellets is identical;

the device does not require an external digitization system. The optically pumped helium magnetometers present on the patient's head make it possible to measure the magnetic field emitted by the three-axis coils and to locate them. The gadolinium pellets are visualized directly on the MRI images;

the patient wears the mask or the thoracic vest during the two types of MEG/MRI or MCG/MRI recording.

The invention is not limited to the embodiments and variants presented, and other embodiments and variants will be clearly apparent to those skilled in the art.

Thus, different sizes of device are envisioned in order to adapt to all age groups (baby, child, adult).

Thus, the dimensions of the supports can vary according to the type of three-axis coil and according to the size of the markers.

The invention claimed is:

1. A device for improving the precision of a biomagnetic image of a patient, the device comprising:
    a covering adapted to be positioned on an anatomical part of the patient;
    a plurality of markers arranged on the covering, the markers being adapted to create a contrast when obtaining an image of the patient produced by magnetic resonance imaging;
    at least five three-axis coils, each three-axis coil being adapted to emit a magnetic field, the magnetic fields of the three-axis coils being detectable by a set of optically pumped magnetometers during an examination by biomagnetic imaging comprising magnetoencephalography (MEG) or magnetocardiography (MCG), the three-axis coils being arranged on the covering so that, when the device is positioned on the patient, each three-axis coil is located on a singular point of the patient; the three-axis coils and markers of the plurality of markers are placed at a same location on the covering so that, when the covering is positioned on the patient, singular points of the anatomical part of the patient are detectable by magnetic resonance imaging and by biomagnetic imaging MEG or MCG, wherein the device comprises supports, each support having a first reception zone adapted to receive one of the markers and a second reception zone adapted to receive one of the three-axis coils, the marker and the three-axis coil then being placed at the same location on the covering, wherein the second reception zone comprises a protuberance adapted to be housed in an associated cavity of the three-axis coil, wherein the protuberance comprises a main body and a pin extending from the main body, the protuberance having the role of an indexing device for positioning the three-axis coil in the support.

2. The device as claimed in claim 1, wherein the covering is made of a flexible biocompatible silicone material.

3. The device as claimed in claim 1, wherein the markers comprise gadolinium and/or a plurality of superparamagnetic nanoparticles.

4. The device as claimed in claim 1, wherein each marker has a shape of a pellet having a diameter of less than or equal to 6 mm.

5. The device as claimed in claim 1, wherein the device is adapted to be positioned on a face of the patient, or wherein the device is adapted to be positioned on a torso of the patient.

6. A method for improving the precision of a biomagnetic image of a patient, the method comprising:
 a step (E1) of applying to a part of the patient a device as claimed in claim 1, the device comprising a plurality of three-axis coils, each three-axis coil being adapted to emit a magnetic field, the magnetic fields of the three-axis coils being detectable by a set of optically pumped magnetometers during a biomagnetic imaging examination comprising magnetoencephalography (MEG) or magnetocardiography (MCG);
 a step (E4) of self-referencing of the position of the optically pumped magnetometers with respect to the three-axis coils;
 a step (E5) of examination by biomagnetic imaging MEG or MCG for obtaining biomagnetic data comprising MEG data or MCG data;
 a step (E6) of examination by magnetic resonance imaging for obtaining MRI data;
 a step (E7) of merging the biomagnetic data comprising MEG data or MCG data with the MRI data by matching of coordinates of common singular points acquired during the biomagnetic imaging examination step and the MRI examination step.

7. The method as claimed in claim 6, wherein the biomagnetic imaging examination is a magnetoencephalography examination for obtaining MEG data or a magnetocardiography examination for obtaining MCG data.

8. The method as claimed in claim 6, wherein the optically pumped magnetometers are optically pumped helium magnetometer.

* * * * *